United States Patent
Liphardt et al.

(10) Patent No.: US 10,066,989 B1
(45) Date of Patent: Sep. 4, 2018

(54) INFORMATION MAINTENANCE, INTENSITY ATTENUATION, AND ANGLE/PLANE OF INCIDENCE CONTROL IN ELECTROMAGENTIC BEAMS

(71) Applicant: J.A. WOOLLAM CO., INC, Lincoln, NE (US)

(72) Inventors: Martin M. Liphardt, Lincoln, NE (US); Ping He, Lincoln, NE (US)

(73) Assignee: J.A. WOOLLAM CO., INC, Lincoln, NE (US)

( * ) Notice: Subject to any disclaimer, the term of this patent is extended or adjusted under 35 U.S.C. 154(b) by 61 days.

(21) Appl. No.: 15/330,353

(22) Filed: Sep. 9, 2016

Related U.S. Application Data (60) Provisional application No. 62/283,911, filed on Sep. 15, 2018.

(51) Int. Cl.
| | |
|---|---|
| *G01J 4/00* | (2006.01) |
| *G01J 3/02* | (2006.01) |
| *G01J 4/04* | (2006.01) |

(52) U.S. Cl.
CPC ........... *G01J 3/0213* (2013.01); *G01J 3/0208* (2013.01); *G01J 3/0224* (2013.01); *G01J 3/0237* (2013.01); *G01J 3/0289* (2013.01); *G01J 4/04* (2013.01)

(58) Field of Classification Search
CPC .......... G01J 4/00; G01J 3/0213; G01J 3/0208; G01J 4/04
USPC ........................................................ 356/367
See application file for complete search history.

(56) References Cited

U.S. PATENT DOCUMENTS

| | | | |
|---|---|---|---|
| 3,905,675 A | 9/1975 | McCracken | |
| 4,877,960 A | 10/1989 | Messerschmidt et al. | |
| 5,042,951 A | 8/1991 | Gold et al. | |
| 5,111,343 A * | 5/1992 | Harrigan | G02B 5/205 |
| | | | 359/885 |
| 5,148,323 A | 9/1992 | Campbell et al. | |
| 5,159,412 A | 10/1992 | Willenborg et al. | |
| 5,166,752 A | 11/1992 | Spanier | |
| 5,373,359 A | 12/1994 | Woollam et al. | |
| 5,504,582 A | 4/1996 | Johs et al. | |
| 5,517,312 A | 5/1996 | Finarov | |
| 5,521,706 A | 5/1996 | Green et al. | |
| 5,608,526 A | 3/1997 | Piwonka-Corle | |
| 5,663,980 A * | 9/1997 | Adachi | H01S 5/02296 |
| | | | 372/103 |
| 5,666,201 A | 9/1997 | Johs et al. | |
| 5,684,642 A | 11/1997 | Zumoto et al. | |

(Continued)

*Primary Examiner* — Roy M Punnoose
(74) *Attorney, Agent, or Firm* — James D. Welch (57) ABSTRACT

A system for providing variable wavelength intensity attenuation to said focused beams by application of an aperture-like element that comprises at least two regions of "filter" material, or comprises different materials graded into one another, which different materials that have different responses to different wavelengths, wherein said system is applied to reduce differences in wavelength intensity levels when applied in collimated portions of a beam as a Spectral Angle Adjustor (SAA) or to preserve information in a beam while changing said beam effective diameter as a Spectral Aperture Stop (SAS); or to affect a Spectral Field Stop (SFS) that controls source image size when applied at a convergent/divergent beam focal point as a Spectrally Varying Aperture, (SVA) the end result depending on where in a beam it is applied.

18 Claims, 8 Drawing Sheets

(56) References Cited

U.S. PATENT DOCUMENTS

| | | | |
|---|---|---|---|
| 5,828,446 A * | 10/1998 | Davis | G01M 11/0214 |
| | | | 356/124 |
| 5,864,139 A * | 1/1999 | Reffner | G01N 21/35 |
| | | | 250/339.05 |
| 5,872,630 A | 2/1999 | Johs et al. | |
| 5,877,859 A | 3/1999 | Aspnes et al. | |
| 5,910,842 A | 6/1999 | Piwonka-Corle | |
| 5,963,327 A | 10/1999 | He et al. | |
| 6,414,804 B1 * | 7/2002 | Yamanaka | G02B 5/22 |
| | | | 359/566 |
| 6,456,435 B1 * | 9/2002 | Cobb | G02B 26/10 |
| | | | 359/577 |
| 6,636,309 B1 | 10/2003 | Johs et al. | |
| 6,690,473 B1 | 2/2004 | Stanke et al. | |
| 6,734,967 B1 | 5/2004 | Piwonka-Corle | |
| 6,738,138 B2 | 5/2004 | Wei | |
| 6,940,595 B1 | 9/2005 | Johs et al. | |
| 7,050,162 B2 | 5/2006 | Opsal et al. | |
| 7,145,654 B2 | 12/2006 | Norton | |
| 7,239,391 B2 | 7/2007 | Synowicki et al. | |
| 7,295,313 B1 | 11/2007 | Johs et al. | |
| 7,336,361 B1 | 2/2008 | Liphardt et al. | |
| 7,345,762 B1 * | 3/2008 | Liphardt | G01N 21/211 |
| | | | 356/369 |
| 7,554,662 B1 | 6/2009 | Liphardt et al. | |
| 7,633,625 B1 * | 12/2009 | Woollam | G01J 3/02 |
| | | | 356/369 |
| 7,671,989 B2 | 3/2010 | Liphardt | |
| 8,351,036 B1 * | 1/2013 | Liphardt | G01J 4/00 |
| | | | 356/369 |
| 8,749,785 B2 * | 6/2014 | Liphardt | G02B 3/00 |
| | | | 356/369 |
| 2002/0097492 A1 * | 7/2002 | Cobb | G02B 26/10 |
| | | | 359/577 |
| 2016/0327779 A1 * | 11/2016 | Hillman | G02B 21/367 |

\* cited by examiner

INFORMATION MAINTENANCE, INTENSITY ATTENUATION, AND ANGLE/PLANE OF INCIDENCE CONTROL IN ELECTROMAGENTIC BEAMS

This Application claims Benefit from Provisional Application No. 62/283,911 Filed Sep. 15, 2015.

TECHNICAL AREA

The present invention relates to focused electromagnetic beams, and more particularly to a system for providing variable wavelength intensity attenuation to said focused beams by application of an aperture-like element that comprises at least two regions of "filter" material, or comprises graded materials that have different responses to different wavelengths, wherein said system is applied to reduce differences in wavelength intensity levels over a spectrum thereof, and/or to control Angle or Plane-of-Incidence of a beam onto a sample when applied in collimated portions of a beam as a Spectral Aperture stop, and/or to control source image size when applied at convergent/divergent beam focal points as a Spectral Field Stop used to effect wavelength dependent beam spot size on a sample, and thereby control light Intensity at Sample by making the Aperture Bigger or Smaller.

BACKGROUND

It is known to attenuate the intensity of electromagnetic beams by applying an aperture or the like in the path thereof when a detector of the beam becomes saturated. This is a straight forward practice where a beam is collimated. However, where a beam is focused, and is caused to impinge on a sample at oblique angles-of-incidence, the practice becomes more complicated. This is because a focused beam arrives at a sample over a range of angles-of-incidence (AOI), with components passing through a focusing element centrally being at a nominal (AOI) and components thereof which pass through the focusing element laterally being at greater or lesser (AOI's). It is noted that there is also a Plane-of-Incidence (POI) associated with a beam's orientation with respect to a sample which presents similar concerns, and can be handled by similar techniques.

U.S. Pat. No. 7,671,989 to Liphardt et al. described applying an aperture to attenuate beam intensity in such a focused beam situation requires that the aperture be positioned so as to preserve the central component, and substantially equal amounts of the greater and lesser (AOI's) to maintain data affecting characteristics in the attenuated beam similar to those in the unattenuated beam.

It is disclosed that the use of aperture elements in reflectometors and ellipsometers and the like is well known in the art. For instance, a Patent to Liphardt et al., U.S. Pat. No. 7,336,361 discloses an ellipsometer system, in FIG. 1b thereof, with five apertures in the pathway of an electromagnetic beam. U.S. Pat. No. 7,554,662 provides, in FIG. 1a6 thereof, a relevant additional Aperture (NAP) prior to a Detector (DET). Said Patents variously show use of a beam of electromagnetic radiation onto a sample, as is the case in the present invention.

Representative Patents which disclose Apertures in an ellipsometer or the like, provided a Patent to Norton, U.S. Pat. No. 7,145,654. The system therein is described as utilizing a beam focused onto the end of an optical fiber, such that the angular range of the probe beam is less than a natural numerical aperture of an optical fiber. The purpose of the Norton invention is to selectively attenuate and reduce the presence of secondary maxima falling outside a measurement spot on a sample. Minimizing said secondary maxima can improve the amount of light measured by a detector that is reflected from inside a measurement spot. Said 654 Patent is included herein by reference.

A U.S. Pat. No. 5,517,312 to Finarov describes application of a scattered light reducing system at the entry to a Detector in a Rotating Analyzer or Rotating Polarizer Ellipsometer System, which scattered light reducing system consists of two lenses with a hole containing diaphram located midway therebetween, and at the focal lengths of said lenses. Said scattered light reducing system is present after a sample system and processes electromagnetic radiation after it interacts with said sample system. The pin-hole is described as serving to reduce scattered light and providing high spatial resolution.

Another Patent identified is that to Campbell et al., U.S. Pat. No. 5,148,323. Said 323 Patent describes a Spatial Filter in which a pinhole is located other than at the focal length of a converging lens.

U.S. Pat. No. 3,905,675 to McCraken describes a Spatial Filter containing system which enables observation of a weak source of electromagnetic radiation in the presence of strong sources thereof.

U.S. Pat. No. 5,684,642 to Zumoto et al., describes an optical transmission system for use in fashioning an electromagnetic beam for use in machining materials which combines a Spatial Filter and an Optical Fiber.

U.S. Pat. No. 4,877,960 to Messerschmidt et al. is identified as it describes masking energy from outside the target area in a microscope having dual remote image masking.

Continuing, Spectroscopic Ellipsometer Systems are also known in the art. Application a Spatial Filters near a Detector, in the context of Rotating Polarizer and Rotating Analyzer Ellipsometer Systems has been reported, (see U.S. Pat. No. 5,517,312 to Finerov). It is noted, that application of Spatial Filters in Rotating Compensator Ellipsometer Systems, such as the Rotating Compensator Ellipsometer System Claimed in co-owned U.S. Pat. No. 5,872,630.

For general reference, a Patent to Dill et al., U.S. Pat. No. 4,053,232 is disclosed as it describes a Rotating-Compensator Ellipsometer System which operates utilizing monochromatic light. Further, a Patent to Aspnes et al., U.S. Pat. No. 5,877,859 is disclosed as it describes a Broadband Spectroscopic Rotating Compensator Ellipsometer System wherein the Utility is derived from selecting a wavelength range and compensator so that at least one wavelength in said wavelength range has a retardation imposed of between 135 and 225 degrees, and another wavelength in said wavelength range has a retardation imposed which is outside that retardation range. Further Patents of general interest of which the Inventors are aware include those to Woollam et al, U.S. Pat. No. 5,373,359, Patent to Johs et al. U.S. Pat. No. 5,666,201 and Patent to Green et al., U.S. Pat. No. 5,521,706, and Patent to Johs et al., U.S. Pat. No. 5,504,582 are disclosed for general information as they pertain to ellipsometer systems. A Patent to He et al., U.S. Pat. No. 5,963,327 is also disclosed as it describes a laterally compact ellipsometer system which enables providing a focused polarized beam of electromagnetic radiation at an oblique angle-of-incidence, and optionally plane-of-incidence to a sample system in a small spot area.

Patents to Piwonka-Corle, U.S. Pat. Nos. 5,608,526, 5,910,842 and 6,734,967 describe focused beam spectroscopic ellipsometer systems which include means for selecting ranges of angles of incidence reflecting from a sample.

Additionally, Patents to Gold, U.S. Pat. No. 5,042,951 and Spanier, U.S. Pat. No. 5,166,752 are disclosed for a similar reason. The present invention differs as no specific guidance as to how to select a range of wavelengths around a nominal angle of incidence to preserve information in a reflected and monitored beam is taught in said Patents.

It is also of interest to note that a computer search for Patents which include both the terms "focused beam" and "aperture" provided only two Patents, namely, U.S. Pat. No. 5,159,412 to Willenborg et al. and U.S. Pat. No. 6,690,473 to Stanke et al., neither of which is particularly relevant to the present invention. Further, U.S. Pat. Nos. 5,910,842, 6,734,967 to Piwonka-Corle et al. are disclosed as they describe use of focused beams in ellipsometry.

Further, as disclosed in Co-pending application Ser. No. 14/545,713, it is known that focusing elements, such as refractive lenses and lens systems, cause both diffraction and aberration to occur in a beam of electromagnetic radiation with which is interacts. It is also known that when the effective diameter of a beam of electromagnetic radiation which impinges on a focusing element is adjusted, the effects of diffraction and of aberration are affected oppositely. That is, as the beam cross-sectional area is increased, the effects of diffraction decrease, but the effects of aberration increase. This leads to a realization that, for each wavelength in the beam, there should be a beam cross-sectional area such that the focusing lens performs "optimally". That is, there exists a cross-section area such that increase or decrease in cross-sectional area will cause combined diffraction or aberration to become worse, (ie. cause lens performance to be worse). Patents identified in said 713 Parent Application are: U.S. Pat. Nos. 7,239,391; 7,295,313; 6,940,595; and 6,636,309. And, said 713 Parent Application also disclosed Patents that use approaches such as apodizing filters, spatial filters, graded lens etc., to improving imaging performance in metrology systems by adjusting the index of lens material index are:

U.S. Pat. No. 6,738,138 to Wei;
U.S. Pat. No. 7,050,162.

Finally, two Patents to Liphardt, U.S. Pat. Nos. 8,351,036 and 8,749,785 are identified as they disclose wavelength dependent materials applied in aperturing.

Even in view of the known art, need remains for a system and method of its use which enables maintenance of beam spot size on a sample, and information content on a focused beam of electromagnetic electromagnetic radiation when the intensity thereof is attenuated by application of an apetrue-like element.

DISCLOSURE OF THE INVENTION

To begin, it is important to understand that the present invention is focused on the application of wavelength dependent materials in systems that can be categorized as Spectral Aperture Stops (SAS) and Spectral Field Stops (SFS), which categories are primarily distinguished as to where in a spectroscopic beam of electromagnetic radiation the wavelength dependent material system is positioned, and therefore the effect they have on said beam. The Spectral Aperture Stop (SAS) is placed in a Collimated part of a spectroscopic beam, while the Spectral Field Stop (SFS) is applied at a convergent/divergent position in a spectroscopic beam, such as after a converging lens. Benefit is derived from the fact that any collimated or convergent region in a spectroscopic beam can be utilized, with the same effect being realized. That is, for instance, it can be easier to access one converent location in a spectroscopic beam than another in, for instance, in an ellipsometer system. It can be easier to access a location before, (or after), a sample depending on a specific system configuration. For emphasis, the present invention can be applied at any of a number of such "conjugate" locations, with the same result. For easy reference the major distinguishing factors in the two categories of the Present Invention, are listed below:

1) Collimated Beam Application Case—Spectral Aperture Stop (SAS)—Two Conditions:
   1) Maintains Information and decreases some Wavelength Intensities to flatten out an Intensity vs. Wavelength Spectrum as a Spectrally variable Aperture (SVA);
   2) Does not deliberately affect Intensity to flatten the Intensity vs. Wavelength Spectrum, and/or focus on Information Maintenance, but rather focus on controlling an effective AOI and/or POI as a Spectral Angle Adjustor (SAA), (eg. by spatial movement along the beam, or replacement thereof).

2) Non-Collimated Bean Application Case—Spectral Field Stop (SFS):
   used as a Spectrally Varying Aperture (SVA) to effect wavelength dependent beam spot size on a sample and thereby control electromagnetic radiation Intensity at Sample by making an effective Filed Stop Aperture Bigger or Smaller. For instance, specific High Intensity wavelengths can be made to have a small spot size by limiting effective Field Stop Aperture size, and Lower Intensity wavelengths can be made to open effective Field Stop Apertures wider to let more light through, but with an accompanying bigger spot size.

Considering first the Spectrally Variable Aperture (SVA) applied in a collimated region of a spectroscopic beam, the most important aspect thereof is that the system of at least two adjacent or graded materials reacts to different wavelengths in a spectroscopic beam of electromagnetic radiation caused to transmit therethrough, differently. It is common for a beam of electromagnetic radiation to be spectroscopic, that is, comprise a multiplicity many different wavelengths. Importantly, it is also typical for the different wavelengths to be present at different Intensity levels. The present invention recognizes this, and that said different intensity levels can cause differences in the results of investigating samples therewith that are not representative of anything about said samples, but are rather artifacts of the spectroscopic beam properties and how detectors react thereto. In this sense the present invention can be thought of as a "Spectrally Variable Aperture (SVA)" in that it presents wavelengths in a spectroscopic beam of electromagnetic radiation that are of relatively lesser Intensity with an effectively larger "aperture diameter", and that presents wavelengths of relatively higher Intensity with an effectively smaller "aperture diameter" based on the "filter-like" properties of the various materials involved that are encountered by said spectroscopic beam of electromagnetic radiation. The benefit is that greater Attenuation can be applied to some wavelengths than to others thereby providing a more uniform Intensity spectrum over a wavelength range. Much like a Silicon/Silicon Dioxide Mirror, (see Patent to Johs et al. U.S. Pat. No. 7,535,566), serves to "smooth-out" the Intensity profile of a Beam of electromagnetic radiation a bit when it reflects therefrom, the present invention provides different attentuation to different wavelength ranges present in a spectroscopic beam of electromagnetic radiation when it is caused to transmit therethrough. The present invention can also be characterized as a system for providing intensity attenuation to a spectroscopic beam of electromagnetic radiation, the locus thereof being oriented to provide a plurality of oblique angles-of-incidence and/or planes-of-incidence to a sample, some greater and some lesser than an average angle-and/or-plane-of-incidence value, while maintaining information therein. That being the case said present invention is related to that in U.S. Pat. No. 7,671,989 to Liphardt et al., in some respects. The present invention is distinguished however, in that the system for providing intensity attenuation to said focused spectroscopic beam in a collimated portion thereof is comprised of at least two regions of different materials, or comprises graded materials that have different responses to different wavelengths.

The present invention can also be applied in a manner that does not deliberately affect Intensity to flatten the Intensity vs. Wavelength Spectrum, and/or focus on Information Maintenance, but rather focus on controlling an effective AOI and/or POI as a Spectral Angle Adjustor (SAA). In this case certain portions of a spectroscopic beam are attenuated more than others.

The present invention can also be applied in a convergent/divergent region of a focused spectroscopic beam and operates as a Spectrally Varying Aperture (SVA) to effect wavelength dependent spectroscopic beam spot size on a sample and thereby control electromagnetic radiation Intensity at Sample by making an effective Filed Stop Aperture Bigger or Smaller. For instance, specific High Intensity wavelengths can be made to have a small spot size by limiting effective Field Stop Aperture size, and Lower Intensity wavelengths can be made to open effective Field Stop Apertures wider to let more light through, but with an accompanying bigger spot size.

The present invention can be applied in reflectometers and spectrophotometers, (and with the addition of polarization state generation and analyzer components, (eg. polarizers and analyzers), ellipsometers and with the addition of at least one compensator, polarimeters), that comprise a source of a spectroscopic beam of electromagnetic radiation and a detector system sequentially positioned such that said source provides a collimated spectroscopic beam of electromagnetic radiation which is caused to become said focused spectroscopic beam, and reflect from said sample before passing through a collimating means and proceeding to said detector system.

Note that the present invention system comprising at least two materials which are adjacent to one another in an effectively stepped manner, or are graded one into the next, can be applied in Collimated regions of the spectroscopic beam as a (SVA) or (SAA), and that there can be Focal Points in a spectroscopic beam between the Source and Detector, other than that which is positioned at the surface of a sample, at which focal point(s) the present invention can be applied as an (SVA).

A present invention system can be described as comprising at least two materials which are adjacent to one another in an effectively stepped manner, or are graded one into the next, such that when a spectroscopic beam of electromagnetic radiation is caused to transmit therethrough toward or away from a sample with which said spectroscopic beam also interacts, different wavelengths in said spectroscopic beam are presented with different attenuation effects as regards wavelength associated intensities, to the end that at least one selection from the group consisting of:

a) for the case wherein the system comprising at least two materials is applied in an essentially collimated region of a spectroscopic beam of electromagnetic radiation, a selection from the group consisting of:
 a1) information contained in the spectroscopic beam of electromagnetic radiation is effectively maintained and at least one wavelength intensity is decreased to flatten out an intensity vs. wavelength spectrum; and
 a2) an angle and/or plane of incidence is controlled for at least on wavelength with information in the spectroscopic beam of electromagnetic radiation not necessarily being maintained;
applies; or
b) for the case wherein the system comprising at least two materials is applied in a convergent/divergent region of a spectroscopic beam of electromagnetic radiation, the system comprising at least two materials is applied to effect wavelength dependent spectroscopic beam spot size on said sample by making the effective field stop aperture presented by said system comprising at least two materials bigger or smaller as a function of wavelength, so that a selection from the group consisting of:
 b1) for at least one relatively high intensity wavelength a relatively small spot size, compared to other wavelength spot sizes compared to other wavelength spot sizes that correspond to at least some lower intensity wavelengths, is achieved on said sample by limiting effective field stop aperture size effected by said system comprising at least two materials; and
 b2) for at least one relatively low intensity wavelength, compared to other wavelengths present, a relatively large spot size, compared to other wavelength spot sizes that correspond to at least some higher intensity wavelengths, is achieved on said sample by expanding an effective field stop aperture size effected by said system comprising at least two materials.

Said present invention system comprising at least two materials can be applied in an essentially collimated region of a spectroscopic beam of electromagnetic radiation and a1) is selected so that information contained in the spectroscopic beam of electromagnetic radiation is effectively maintained and at least one wavelength intensity is decreased to flatten out an intensity vs. wavelength spectrum.

Said present invention system comprising at least two materials can be applied in an essentially collimated region of a spectroscopic beam of electromagnetic radiation and a2) is selected so that an angle and/or plane of incidence is controlled for at least on wavelength with information in the spectroscopic beam of electromagnetic radiation not necessarily being maintained.

Said present invention system comprising at least two materials can be applied in an essentially collimated region of a spectroscopic beam of electromagnetic radiation and b1) is selected so that for at least one relatively high intensity wavelength, compared to other wavelengths spot sizes that correspond to at least some lower intensity wavelengths present, a relatively small spot size is achieved on said sample by limiting effective field stop aperture size effected by said system comprising at least two materials.

Said present invention system comprising at least two materials can be applied in an essentially collimated region of a spectroscopic beam of electromagnetic radiation and b2) is selected so that for at least one relatively low intensity wavelength, compared to other wavelengths present, a relatively large spot size, compared to wavelength spot sizes that correspond to at least some higher intensity wavelengths, is achieved on said sample by expanding an effective field stop aperture size effected by said system comprising at least two materials.

Said present invention system can further comprise a source of a spectroscopic beam of electromagnetic radiation and a detector system sequentially positioned such that said source provides a collimated spectroscopic beam of electromagnetic radiation which is caused to become said focused spectroscopic beam, and reflect from said sample before passing through a collimating means and proceeding to said detector system;

where said system is a reflectometer, spectrophotometer or ellipsometer.

A present invention method of automatically controlling characteristics of a sample investigating spectroscopic beam of electromagnetic radiation comprising the steps of:
1) providing a system as described above;
2) causing a beam of spectroscopic radiation to interact with said provided system and exit therefrom, said exiting spectroscopic beam being characterized by a selection from the group consisting of:
    a) for the case wherein the system comprising at least two materials is applied in an essentially collimated region of a spectroscopic beam of electromagnetic radiation, a selection from the group consisting of:
        a1) information contained in the spectroscopic beam of electromagnetic radiation is effectively maintained and at least one wavelength intensity is decreased to flatten out an intensity vs. wavelength spectrum; and
        a2) an angle and/or plane of incidence is controlled for at least on wavelength with information in the spectroscopic beam of electromagnetic radiation not necessarily being maintained;
    applies; or
    b) for the case wherein the system comprising at least two materials is applied in a convergent/divergent region of a spectroscopic beam of electromagnetic radiation, the system comprising at least two materials is applied to effect wavelength dependent spectroscopic beam spot size on said sample by making the effective field stop aperture presented by said system comprising at least two materials bigger or smaller as a function of wavelength, so that:
        b1) for at least one relatively high intensity wavelength, compared to other wavelength spot sizes that correspond to at least some lower intensity wavelengths, a relatively small spot size is achieved on said sample by limiting effective field stop aperture size effected by said system comprising at least two materials; and
        b2) for at least one relatively low intensity wavelength, compared to other wavelengths present, a relatively large spot size, compared to other wavelength spot sizes that correspond to at least some higher intensity wavelengths, is achieved on said sample by expanding an effective field stop aperture size effected by said system comprising at least two materials;
    applies;
said method further comprising causing a detector to intercept said spectroscopic beam and providing sample characterizing data.

As in the case for the system, said method can be practiced in line with a specific selection from the group of a1), a2), b1) and b2).

Further, said method can further provide that the system comprises a source of a spectroscopic beam of electromagnetic radiation, a polarization state generator, a polarization state analyzer and a detector system sequentially positioned such that said source provides a collimated spectroscopic beam of electromagnetic radiation which is directed to pass through said a polarization state generator, then become said focused spectroscopic beam and reflects from said sample before passing through a collimating means and said polarization state analyzer and proceeding to said detector system; where said system is an reflectometer, spectrophotometer, ellipsometer or polarimeter.

It is also to be understood that the present invention can include the case where at least two systems, each comprising at least two materials which are adjacent to one another in an effectively stepped manner, or are graded one into the next, cn be present and a present invention can include both thereof, one in a collimated, and one in convergent/divergent region of a spectroscopic beam of electromagnetic radiation.

Finally, the whole process can be automated so that, for instance, a saturated detector provides a signal to effect information maintaining attenuation, and then, with said attenuating entered in a way that preserves, if desired, the average angle and/or plane-of-incidence, and plane-of-incidence proceed to acquire data.

The present invention will be better understood by reference to the Detailed Description Section of this Specification.

BRIEF DESCRIPTION OF THE DRAWINGS

FIG. 2A1 shows a beam cross-section of an unattenuated beam.

FIG. 2A2 shows a plot of a parameter, (eg. AOI), of the beam in FIG. 2A1.

FIG. 2B1 shows a beam cross-section of an attenuated beam.

FIG. 2B2 shows a plot of a parameter, (eg. AOI), of the beam in FIG. 2Bb1.

FIG. 7A1 shows an aperture arrangement wherein there is a central opening (OP) and, radially, two different materials (MA) and (ST) that respond to different wavelengths differently.

FIG. 7A2 shows and aperture arrangement wherein there is a central opening (OP) and, radially, three different materials (MA) (MB) and (ST) that respond to different wavelengths differently.

DETAILED DESCRIPTION

Figure 6A:
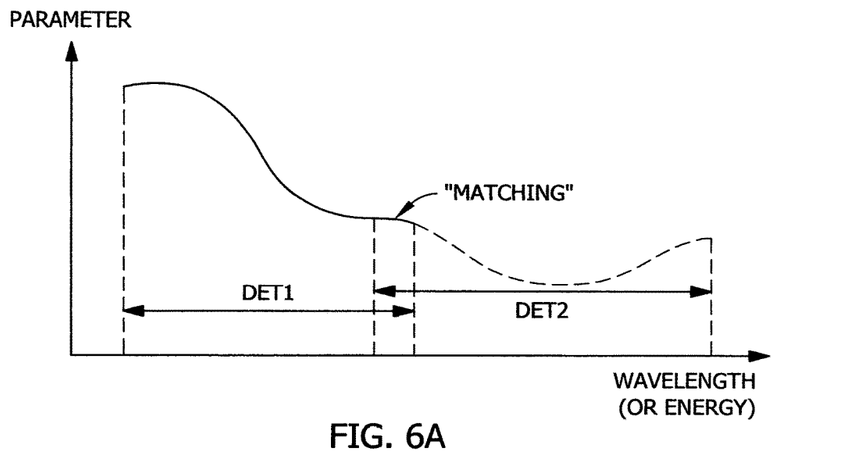
FIG. 6A shows a plot of data obtained from a system as in FIG. 5, showing that where attenuation is properly applied data in an overlap range of wavelengths matches.
Figure 6B:
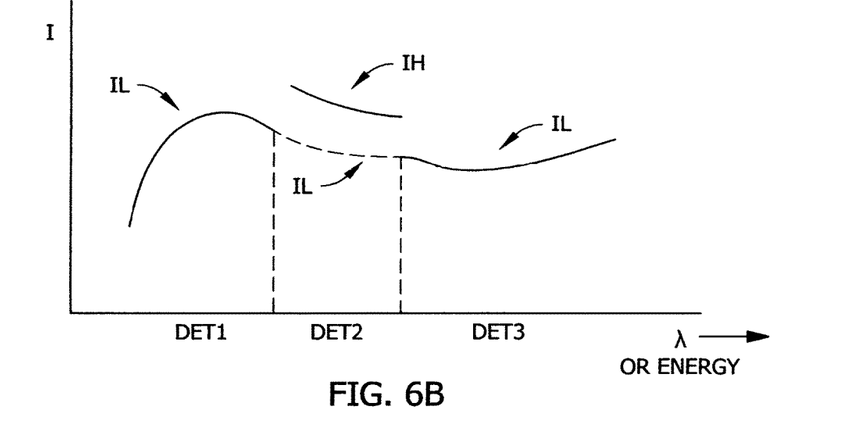
FIG. 6B demonstrates that a mid-region, for instance, of wavelengths in a spectroscopic beam of electromagnetic radiation that enter a Detector (DET2) can be of higher intensity than wavelengths on either side thereof which enter Detectors (DET1) and (DET3).
Figure 7A:
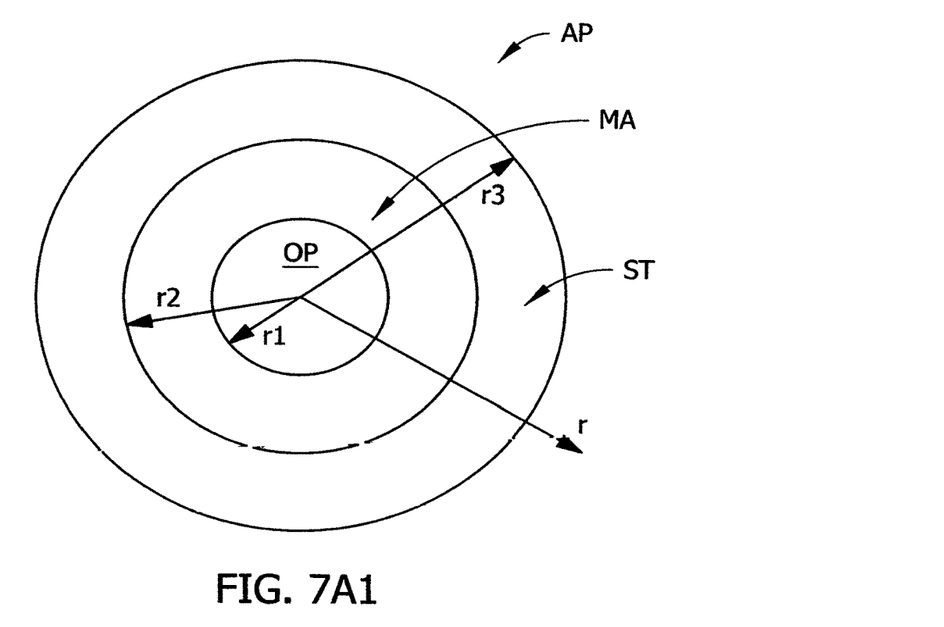

The Figures are to be considered in view of the present invention, which in it's most straight forward embodiment, comprises the application of a system comprising at least two materials, (see variously (MA) (MB) (ST) in FIGS. 7A1 and 7A2), which are adjacent to one another in an effectively stepped manner, or are graded one into the next. When a collimated region of a spectroscopic beam of electromagnetic radiation (see (COL) in FIGS. 9A and 9B), is caused to transmit therethrough, different wavelengths in said spectroscopic beam are presented with different effective aperture diameters and hence with different effects on wavelength associated intensities, to the end that the spectroscopic beam exiting said system can present a relatively more constant intensity v. wavelength profile than that entering, (see FIGS. 6B and 6A for an application to dual detectors (DET1), (DET2), with accompanying information content preservation, (enabled by application of symmetrically applied systems as in FIGS. 3B, 3D, 7A1 and 7A2), or the Angle or Plane-of-Incidence is controlled without attention necessarily being paid to information content preservation, (enabled by non-symmetrical application of systems such as in FIGS. 3A and 3C). Such application can be achieved by placing the present invention system at a converging/diverging location in a focused spectroscopic beam, (see placement of (SVA) in FIGS. 9A and 9B at a convergent/divergent spectroscopic beam location).

Figure 9A:
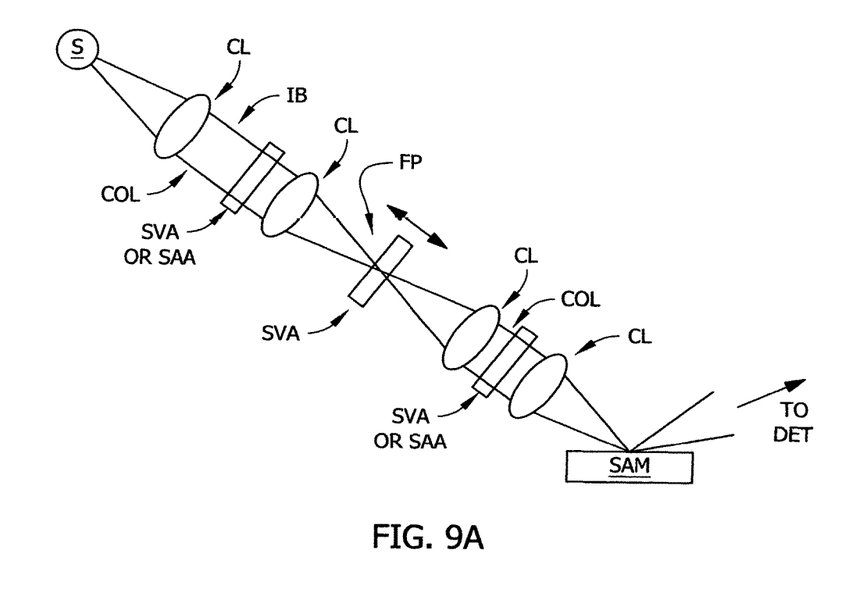
FIG. 9A shows application of a system of at least two materials or graded materials to a converging/diverging region of a spectroscopic beam near a focus point thereof, to form a "Spectrally Varying Aperture" near said focus point.
Figure 9B:
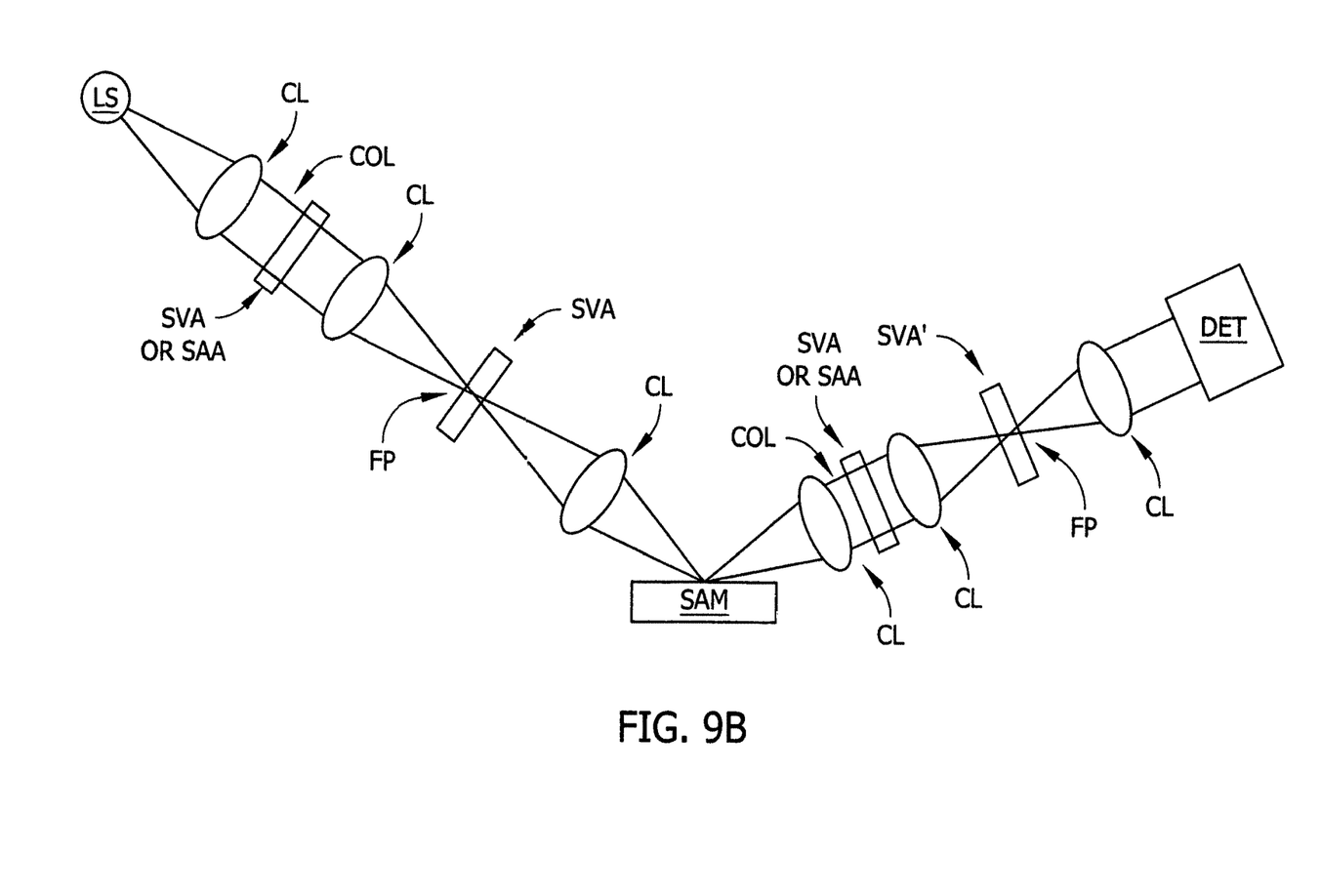
FIG. 9B is included to indicate that anywhere that a spectroscopic beam is directed to a Focal Point (FP) between the Source (S) and Detector (DET), (without impinging on a Sample (SAM)), a "Spectrally Varying Aperture" can be utilized near said Focal Point (FP).

Said present invention system, can then be applied as an (SVA) in a region in which spectroscopic beam controlling optics provide substantially collimated region(s) in the spectroscopic beam, (see placement of (SVA) in FIGS. 9A and 9B at collimated locations in said spectroscopic beam). It is also possible to place a Spectral Angle Adjustor (SAA) at said locations in a collimated portion of said spectroscopic beam, such as is made possible by systems such as those in FIG. 3A. When so applied in said substantially collimated regions thereby forming a "Spectral Angle Adjustor" (SAA) that serves to change intensity of various wavelength components in a nonsymmetrical way that focuses on changing Angle or Plane of Incidence (AOI and/or POI), rather than on maintaining an average AOI so as to preserve information in the spectroscopic beam.

Figure 7A:
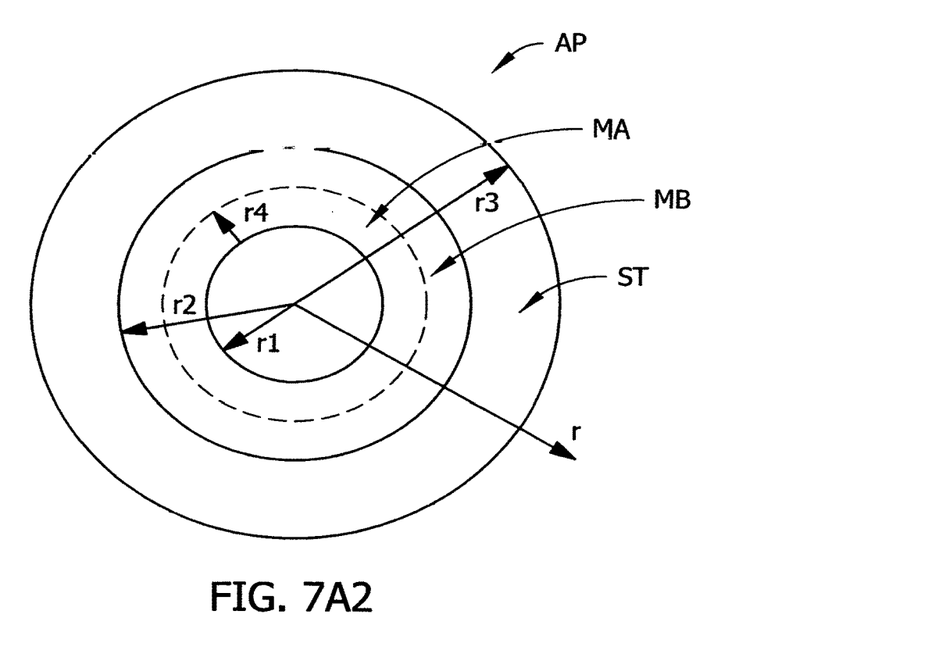

FIG. 7A1 shows a present invention aperture arrangement wherein there is a central opening (OP) and, radially, two different materials (MA) and (ST) that respond to different wavelengths differently. In the present invention (MA) would typically be opaque for wavelengths that have higher Intensities, and at least semitransparent for wavelengths that have relatively lower Intensities. (ST) is typically an opaque material at all wavelengths. Also, FIG. 7A2 shows an aperture arrangement wherein there is a central opening (OP) and, radially, three different materials (MA) (MB) and (ST) that respond to different wavelengths differently. In the present invention (MA) would typically be opaque for wavelengths that have higher Intensities, and at least semi-transparent for wavelengths that have relatively lower Intensities. The additional material (MB) allows better precision in tailoring material response to various wavelengths to increase effective at least semitransparency for wavelengths with relatively lower Intensities, and an opaque response for wavelengths at which Intensity is relatively greater. Again, (ST) is typically an opaque material at all wavelengths.

Figure 1:
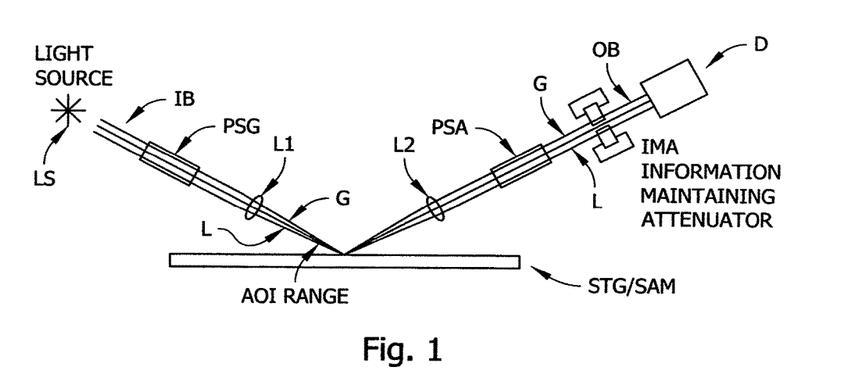
FIG. 1 shows an ellipsometer system with a focused electromagnetic beam.

Turning now to FIG. 1, there is shown a demonstrative ellipsometer system using a focused electromagnetic spectroscopic beam. Shown are a Source (LS) of a spectroscopic beam of electromagnetic radiation, a Polarization State Generator (PSG), a First Focusing Means (L1), a Stage and Sample (STG/SAM), a Collimation Means (L2), a Polarization State Analyzer (PSA) and a Detector (DET). The system also comprises an Information Maintaining Attenuator (IMA), so called as it can perform as an Spectroscopic Variable Aperture Stops (SVA). Note that the (IMA) can be applied as a (SAA), as in both cases it is present in a substantially collimated region of the spectroscopic electromagnetic beam (OB).

In use the spectroscopic beam of electromagnetic radiation passing through the Information Maintaining Attenuator (IMA) and into the Detector (DET) might be of too high an intensity and saturate the Detector electronics. This might happen where a Sample is very reflective, for instance. In such as case the (IMA) can be operated to block some of the Output Beam (OB). This might be accomplished by, for instance, placing a smaller opening aperture in place, or operating an effective Iris. Importantly, it is specifically noted that the focused spectroscopic beam (IB) has components with Greater (G) and Lesser (L) (AOI's). In that light it is noted that the element identified as (IMA) can be applied to eliminate some thereof when it operates as a (SAA), thereby controlling the Angle of Incidence.

It is noted that if the Polarization State Generator (PSG) and Polarization State Analyzer (PSA) are removed from FIG. 1, the result is a Reflectometer.

Figures 2A, 2A, 2A:
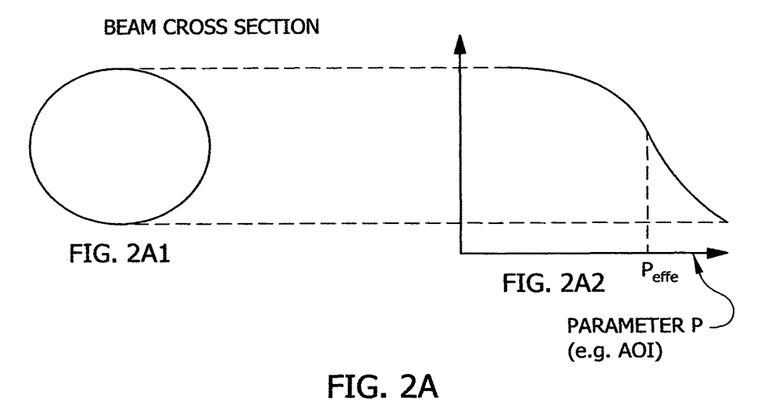
Figures 2B, 2B, 2B:
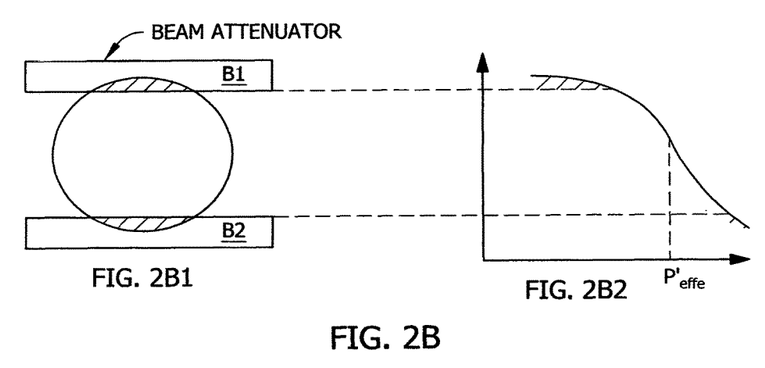

Continuing, FIG. 2A1 shows a beam cross-section of an unattenuated beam and FIG. 2A2 shows a plot of a parameter, (eg. AOI), of the beam in FIG. 2A1. Note in particular that an average location (Peff) is indicated. Now, FIG. 2B1 shows a beam cross-section of an attenuated beam and FIG. 2B2 shows a plot of a parameter, (eg. AOI), of the beam in FIG. 2B1. Note again that there is an associated average location (Peff'). If the (IMA) is symmetrically applied to equally block Greater (G) and Lesser (L) (AOI) components then (Peff) and (Peff') will be equal. This point is at the heart of the present invention where a Spectrally Variable Aperture Stop (SVA) is applied to the beam of FIG. 2B1. Note that the materials (B1) and (B2) comprise at least two materials, which are adjacent to one another in an effectively stepped manner, or are graded one into the next. Different wavelengths will be affected differently as a result, but in the case of FIGS. 2A2 and 2B2, the Peffe and Peffe' will be the same for a specific wavelength.

Figure 3A:
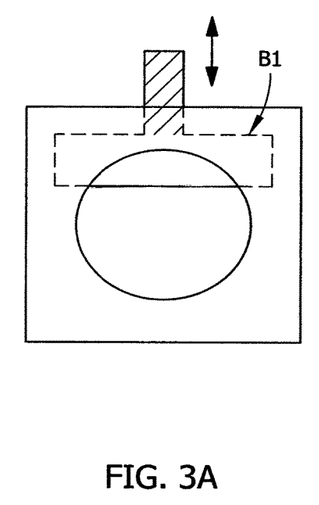
FIGS. 3A-3D show various embodiments of beam attenuation elements.
Figure 3B:
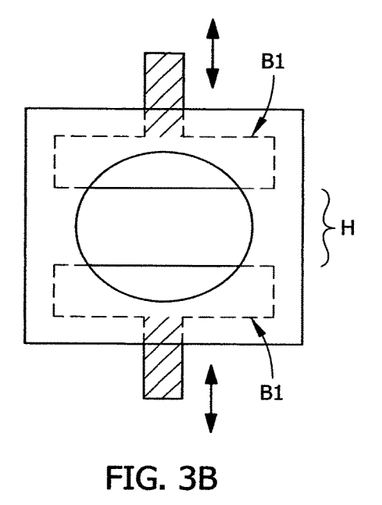
Figure 3C:
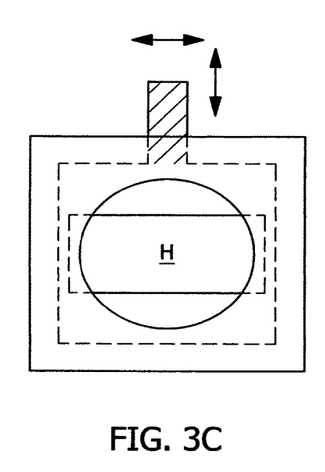
Figure 3D:
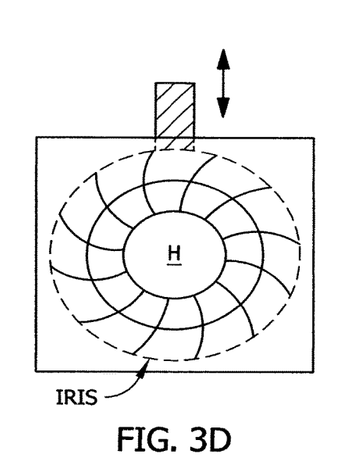
Figure 4:
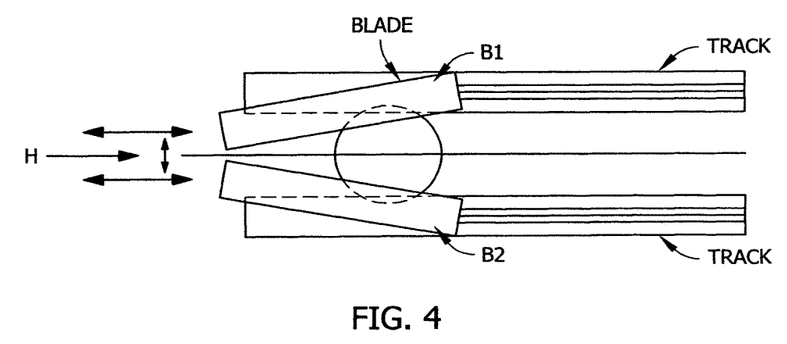
FIG. 4 shows a knife-edge system for controlling beam attenuation.

FIGS. 3A-3D show various embodiments of spectroscopic beam attenuation elements. FIG. 3A shows a single sided Beam Blocking element (B1), which can be used as an asymmetrical (SAA), and FIG. 3B shows a double Beam Blocking element system (B1) (B2). Again, (B1) is comprises at least two materials, which are adjacent to one another in an effectively stepped manner, or are graded one into the next. FIG. 3C shows a rectangular shaped opening (H) in a single Beam Blocking element, which rectangular shaped (H) opening can be moved with respect to the Beam cross-section and again can be used as a (SAA). FIG. 3D shows an Iris Beam Blocking element with a circular (H) suitable for use as a symmetrical (SVA). The present invention achieves similar results by application of a system that comprises at least two materials, which are adjacent to one another in an effectively stepped manner, or are graded one into the next. Different wavelengths will be affected differently as a result. FIG. 4 shows an effective dual knife-edge system for controlling spectroscopic beam attenuation from the top and bottom of a spectroscopic beam. Note an effective Hole (H) is formed by the edges of the two Blades (B1) (B2). The present invention achieves a similar result, but applies a Spectrally Variable Aperture Stop (SVA) applied in a collimated region of a spectroscopic beam, wherein a system of at least two adjacent or graded materials reacts to different wavelengths in a spectroscopic beam of electromagnetic radiation caused to transmit therethrough, differently.

Figure 5:
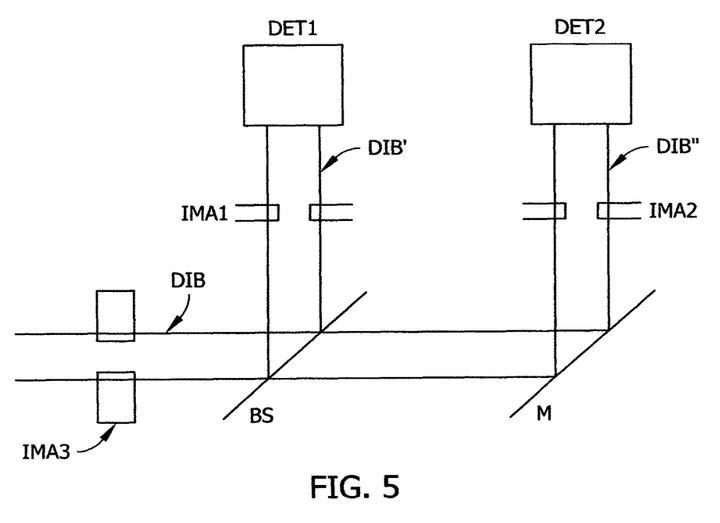
FIG. 5 shows a multiple detector system wherein different ranges of wavelengths are caused to enter different detectors, including intensity attenuation elements.

FIG. 5 shows a multiple detector system wherein different ranges of wavelengths are caused to enter different detectors, including intensity attenuation elements. Shown are a Detector Input Beam (DIB) which passes through Information Maintaining Attenuator (IMA3) before being partially passed and partially reflected by Beam Splitter (BS). The reflected part of (DIB) enters the First Detector (DET1) via Information Maintaining Attenuator (IMA1) and the transmitted part of (DIB) enters the Second Detector (DETs) via Information Maintaining Attenuator (IMA2) after reflection from Mirror (M). FIG. 6A shows that if Attenuation providing means are properly adjusted, a plot of some Parameter, (eg. Intensity), vs. Wavelength obtained partially from Detector (DET1) and partially from Detector (DET2) will provide the same data where the Wavelengths monitored overlap. FIG. 6B demonstrates that a mid-region, for instance, of wavelengths in a beam of electromagnetic radiation that enter a Detector (DET2) can be of higher intensity than wavelengths on either side thereof which enter Detectors (DET1) and (DET3). The present invention system as exemplified in FIGS. 7A1 and 7A2 can be applied to present a small effective transmissive aperture radius (r) to the mid-range wavelengths than it does to the shorter and longer wavelengths, thereby reducing the mid-range wavelength intensity. That is, the mid-range wavelengths (IH) can be reduced to (IL) so that a continuous plot is achieved. It is emphasized that the higher (IH) intensity in the mid-range wavelengths is not indicating any sample relevant effects. It is fully an artifact caused by spectroscopic beam characteristics. The present invention system corrects for this and enables a continuous (IL) plot over the entire relevant wavelength range. FIGS. 7A1 and 7A2 were presented earlier in this Detailed Description.

Figure 8:
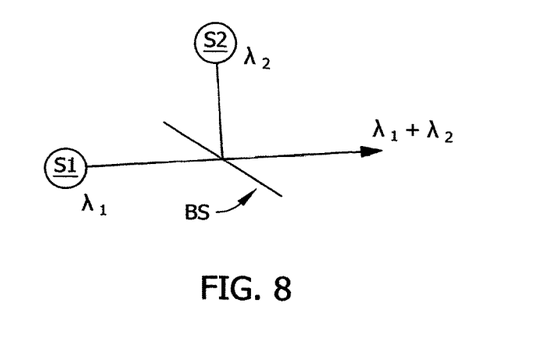
FIG. 8 shows how multiple sources that provide different wavelengths can be combined into a single spectroscopic beam.

FIG. 8 shows how multiple sources that provide different wavelengths can be combined into a single spectroscopic beam by application of a Beam Splitter (BS). Such an arrangement allows forming a source having a greater wavelength range.

FIG. 9A shows application of a system of at least two materials or graded materials to a converging/diverging region of a spectroscopic beam near a focus point thereof, to form a "Spectrally Varying Aperture" (SVA) near said focus point (FP). (See also (SVA') in FIG. 9B). FIG. 9B is included to indicate that anywhere that a spectroscopic beam is directed to a Focal Point (FP) between the Source (S) and Detector (DET), (without impinging on a Sample (SAM)), a "Spectrally Varying Aperture" (SVA) can be utilized near said Focal Point (FP). Also shown are "Spectral Angle Adjustor" (SAA). "Spectrally Varying Apertures (SVA) (SVA') and Spectral Angle Adjustors" (SAA) are better discussed in the Disclosure of the Invention Section of this Specification. as are Spectral Angle Stops (SAS).

Finally, it is noted that while the disclosure used angle-of-incidence as a primary example, planes-of-incidence can also be adjusted likewise so that equal amounts of greater and lesser than an average plane-of-incidence spectroscopic beam components are blocked, such that an average plane-of-incidence for both the unattenuated and attenuated spectroscopic beams are equal. The Claims should be read to cover the angle of incidence, optionally including the plane of incidence.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. At least one system comprising at least two materials which are adjacent to one another in an effectively stepped manner, or are graded one into the next, such that when a spectroscopic beam of electromagnetic radiation is caused to transmit therethrough toward or away from a sample with which said spectroscopic beam also interacts, different wavelengths in said spectroscopic beam are presented with different attenuation effects as regards wavelength associated intensities, to the end that at least one selection from the group consisting of:

a) for the case wherein the system comprising at least two materials is applied in a collimated, or at least substantially collimated region of a spectroscopic beam of electromagnetic radiation, a selection from the group consisting of:
   a1) information contained in the spectroscopic beam of electromagnetic radiation is effectively maintained and at least one wavelength intensity is decreased to flatten out an intensity vs. wavelength spectrum; and
   a2) an angle and/or plane of incidence is controlled for at least on wavelength with information in the spectroscopic beam of electromagnetic radiation not necessarily being maintained;

applies; and b) for the case wherein the system comprising at least two materials is applied in a convergent/divergent region of a spectroscopic beam of electromagnetic radiation, the system comprising at least two materials is applied to effect wavelength dependent spectroscopic beam spot size on said sample by making the effective field stop aperture presented by said system comprising at least two materials bigger or smaller as a function of wavelength, so that a selection from the group consisting of:
   b1) for at least one relatively high intensity wavelength a relatively small spot size, compared to other wavelength spot sizes that correspond to at least some lower intensity wavelengths, is achieved on said sample by limiting effective field stop aperture size effected by said system comprising at least two materials; and
   b2) for at least one relatively low intensity wavelength, compared to other wavelengths present, a relatively large spot size, compared to other wavelength spot sizes that correspond to at least some higher intensity wavelengths, is achieved on said sample by expanding an effective field stop aperture size effected by said system comprising at least two materials;

applies;

said system being characterized in that, in either case a) or b) there is no additional element directly associated with and adjacent to the at least one system comprising at least two materials.

2. At least one system as in claim 1, in which there are present at least two systems, each comprising at least two materials, wherein one said system is present in a collimated, or at least substantially collimated region of a spectroscopic beam of electromagnetic radiation, and another is present in a convergent/divergent portion of the spectroscopic beam of electromagnetic radiation.

3. At least one system as in claim 1, in which the system comprising at least two materials is applied in a collimated or at least substantially collimated region of a spectroscopic beam of electromagnetic radiation and a1) is selected so that information contained in the spectroscopic beam of electromagnetic radiation is effectively maintained and at least one wavelength intensity is decreased to flatten out an intensity vs. wavelength spectrum.

4. A system as in claim 1, in which the system comprising at least two materials is applied in a collimated, or at least substantially collimated region of a spectroscopic beam of electromagnetic radiation and a2) is selected so that an angle and/or plane of incidence is controlled for at least on wavelength with information in the spectroscopic beam of electromagnetic radiation not necessarily being maintained.

5. A system as in claim 1, in which the system comprising at least two materials is applied in a convergent/divergent region of a spectroscopic beam of electromagnetic radiation and b1) is selected so that for at least one relatively high intensity wavelength, compared to other wavelengths spot sizes that correspond to at least some lower intensity wavelengths present, a relatively small spot size is achieved on said sample by limiting effective field stop aperture size effected by said system comprising at least two materials.

6. A system as in claim 1, in which the system comprising at least two materials is applied in a convergent/divergent region of a spectroscopic beam of electromagnetic radiation and b2) is selected so that for at least one relatively low intensity wavelength, compared to other wavelengths present, a relatively large spot size, compared to wavelength spot sizes that correspond to at least some higher intensity wavelengths, is achieved on said sample by expanding an effective field stop aperture size effected by said system comprising at least two materials.

7. A system as in claim 1, which further comprises a source of a spectroscopic beam of electromagnetic radiation and a detector system sequentially positioned such that said source provides a collimated spectroscopic beam of electromagnetic radiation which is caused to become said focused spectroscopic beam, and reflect from said sample before passing through a collimating means and proceeding to said detector system;
where said system is a reflectometer.

8. A system as in claim 1, which further comprises a source of a spectroscopic beam of electromagnetic radiation, a polarization state generator, a polarization state analyzer and a detector system sequentially positioned such that said source provides a collimated spectroscopic beam of electromagnetic radiation which is directed to pass through said a polarization state generator, then become said focused spectroscopic beam and reflects from said sample before passing through a collimating means and said polarization state analyzer and proceeding to said detector system;
where said system is an spectrophotometer.

9. A system as in claim 1, which further comprises a source of a spectroscopic beam of electromagnetic radiation, a polarization state generator, a polarization state analyzer and a detector system sequentially positioned such that said source provides a collimated spectroscopic beam of electromagnetic radiation which is directed to pass through said a polarization state generator, then become said focused spectroscopic beam and reflects from said sample before passing through a collimating means and said polarization state analyzer and proceeding to said detector system;
where said system is an ellipsometer or polarimeter.

10. A method comprising automatically controlling characteristics of a sample investigating spectroscopic beam of electromagnetic radiation comprising the steps of:
1) providing at least one system comprising:
at least two materials which are adjacent to one another in an effectively stepped manner, or are graded one into the next, such that when a spectroscopic beam of electromagnetic radiation is caused to transmit therethrough toward or away from a sample with which said spectroscopic beam also interacts, different wavelengths in said spectroscopic beam are presented with different attenuation effects as regards wavelength associated intensities, to the end that at least one selection from the group consisting of:
a) for the case wherein the at least one system comprising at least two materials is applied in a collimated, or at least substantially collimated region of a spectroscopic beam of electromagnetic radiation, a selection from the group consisting of:
a1) information contained in the spectroscopic beam of electromagnetic radiation is effectively maintained and at least one wavelength intensity is decreased to flatten out an intensity vs. wavelength spectrum; and
a2) an angle and/or plane of incidence is controlled for at least on wavelength with information in the spectroscopic beam of electromagnetic radiation not necessarily being maintained;
applies; and
b) for the case wherein the at least one system comprising at least two materials is applied in a convergent/divergent region of a spectroscopic beam of electromagnetic radiation, the system comprising at least two materials is applied to effect wavelength dependent spectroscopic beam spot size on said sample by making the effective field stop aperture presented by said system comprising at least two materials bigger or smaller as a function of wavelength, so that, a selection from the group consisting of:
b1) for at least one relatively high intensity wavelength a relatively small spot size, compared to other wavelength spot sizes that correspond to at least some lower intensity wavelengths, is achieved on said sample by limiting effective field stop aperture size effected by said system comprising at least two materials; and
b2) for at least one relatively low intensity wavelength a relatively large spot size is, compared to other wavelength spot sizes that correspond to at least some higher intensity wavelengths, achieved on said sample by expanding an effective field stop aperture size effected by said system comprising at least two materials;
applies;
said system being characterized in that, in either case a) or b) there is no additional element directly associated with and adjacent to the at least one system comprising at least two materials:
2) causing a spectroscopic beam of spectroscopic radiation to interact with said provided at least one system and exit therefrom, said exiting spectroscopic beam being characterized by a selection from the group consisting of:
a) for the case wherein the at least one system comprising at least two materials is applied in a collimated, or at least substantially collimated region of a spectroscopic beam of electromagnetic radiation, a selection from the group consisting of:
  a1) information contained in the spectroscopic beam of electromagnetic radiation is effectively maintained and at least one wavelength intensity is decreased to flatten out an intensity vs. wavelength spectrum; and
  a2) an angle and/or plane of incidence is controlled for at least on wavelength with information in the spectroscopic beam of electromagnetic radiation not necessarily being maintained;
applies;
b) for the case wherein the at least one system comprising at least two materials is applied in a convergent/divergent region of a spectroscopic beam of electromagnetic radiation, the system comprising at least two materials is applied to effect wavelength dependent beam spot size on said sample by making the effective field stop aperture presented by said system comprising at least two materials bigger or smaller as a function of wavelength, so that:
  b1) for at least one relatively high intensity wavelength, compared to other wavelength spot sizes that correspond to at least some lower intensity wavelengths, a relatively small spot size is achieved on said sample by limiting effective field stop aperture size effected by said system comprising at least two materials; and
  b2) for at least one relatively low intensity wavelength, compared to other wavelengths present, a relatively large spot size, compared to other wavelength spot sizes that correspond to at least some higher intensity wavelengths, is achieved on said sample by expanding an effective field stop aperture size effected by said system comprising at least two materials;
applies;
said method further comprising causing a detector to intercept said beam and providing sample characterizing data.

11. A method as in claim 10, in which there are present at least two systems, each comprising at least two materials, one of which systems is applied in a collimated or substantially collimated region of a beam of electromagnetic radiation, and another thereof is applied in a convergent/divergent portion of the spectroscopic beam of electromagnetic radiation.

12. A method as in claim 10, in which the system comprising at least two materials is applied in a collimated, or at least substantially collimated region of a beam of electromagnetic radiation and a1) is selected so that information contained in the spectroscopic beam of electromagnetic radiation is effectively maintained and at least one wavelength intensity is decreased to flatten out an intensity vs. wavelength spectrum.

13. A method as in claim 10, in which the system comprising at least two materials is applied in a collimated, or at least substantially collimated region of a beam of electromagnetic radiation and a2) is selected so that an angle and/or plane of incidence is controlled for at least on wavelength with information in the spectroscopic beam of electromagnetic radiation not necessarily being maintained.

14. A method as in claim 10, in which the system comprising at least two materials is applied in a convergent/divergent region of a beam of electromagnetic radiation and b1) is selected so that for at least one relatively high intensity wavelength, compared to other wavelengths spot sizes that correspond to at least some lower intensity wavelengths present, a relatively small spot size is achieved on said sample by limiting effective field stop aperture size effected by said system comprising at least two materials.

15. A method as in claim 10, in which the system of at least two materials is applied in a convergent/divergent region of a beam of electromagnetic radiation and b2) is selected so that for at least one relatively low intensity wavelength, compared to other wavelengths present, a relatively large spot size, compared to wavelength spot sizes that correspond to at least some higher intensity wavelengths, is achieved on said sample by expanding an effective field stop aperture size effected by said system comprising at least two materials.

16. A method as in claim 10, which further comprises a source of a beam of electromagnetic radiation and a detector system sequentially positioned such that said source provides a collimated beam of electromagnetic radiation which is caused to become said focused beam, and reflect from said sample before passing through a collimating means and proceeding to said detector system;
where said system is a reflectometer.

17. A method as in claim 10, which further comprises a source of a beam of electromagnetic radiation, a polarization state generator, a polarization state analyzer and a detector system sequentially positioned such that said source provides a collimated beam of electromagnetic radiation which is directed to pass through said a polarization state generator, then become said focused beam and reflects from said sample before passing through a collimating means and said polarization state analyzer and proceeding to said detector system;
where said system is an spectrophotometer.

18. A method as in claim 10, which further comprises a source of a beam of electromagnetic radiation, a polarization state generator, a polarization state analyzer and a detector system sequentially positioned such that said source provides a collimated beam of electromagnetic radiation which is directed to pass through said a polarization state generator, then become said focused beam and reflects from said sample before passing through a collimating means and said polarization state analyzer and proceeding to said detector system;
where said system is an ellipsometer or polarimeter.

* * * * *